United States Patent [19]

Fukuma et al.

[11] Patent Number: 5,058,556
[45] Date of Patent: Oct. 22, 1991

[54] DEVICE FOR DETERMINING ACTIVATED CONDITION OF AN OXYGEN SENSOR

[75] Inventors: Takao Fukuma; Keisuke Tsukamoto; Toshio Takaoka; Hirofumi Yamasaki, all of Toyota, Japan

[73] Assignee: Toyota Jidosha Kabushiki Kaisha, Toyota, Japan

[21] Appl. No.: 638,844

[22] Filed: Jan. 8, 1991

[30] Foreign Application Priority Data

Jan. 23, 1990 [JP] Japan ................... 2-14193

[51] Int. Cl.$^5$ ............................................. F02D 41/14
[52] U.S. Cl. ................................................... 123/489
[58] Field of Search ............... 123/325, 326, 440, 489, 123/479; 204/406, 425, 426, 427, 428

[56] References Cited

U.S. PATENT DOCUMENTS

| | | | |
|---|---|---|---|
| 4,186,691 | 2/1980 | Takase et al. | 123/325 |
| 4,648,370 | 3/1987 | Kobayashi et al. | 123/326 X |
| 4,707,241 | 11/1987 | Nakagawa et al. | 123/489 X |
| 4,723,521 | 2/1988 | Mieno et al. | 123/489 |
| 4,724,814 | 2/1988 | Mieno et al. | 123/489 X |
| 4,759,328 | 7/1988 | Blumel et al. | 123/489 X |
| 4,958,612 | 9/1990 | Kato et al. | 123/489 |
| 4,964,271 | 10/1990 | Sawada et al. | 123/489 X |
| 4,981,122 | 1/1991 | Osawa et al. | 123/325 |

FOREIGN PATENT DOCUMENTS

59-46350  3/1984  Japan .
60-212650 10/1985  Japan .

Primary Examiner—Willis R. Wolfe
Attorney, Agent, or Firm—Kenyon & Kenyon

[57] ABSTRACT

A device for determining an activated condition of the oxygen sensor of a lean sensor for an electric-controlled fuel injection internal combustion engine. When the engine is under a fuel cut operation, the output level from the oxygen sensor is compared with a first predetermined threshold level or with a second predetermined threshold level which is lower than the first threshold level. A determination of the activated condition of the oxygen sensor is obtained when the output level from the oxygen once exceeds the higher first level, or when the output level from the oxygen sensor consecutively exceeds the higher first level twice, whereby a positive and quick determination of the activated condition of the oxygen sensor can be obtained.

3 Claims, 7 Drawing Sheets

DEVICE FOR DETERMINING ACTIVATED CONDITION OF AN OXYGEN SENSOR

BACKGROUND OF THE INVENTION

1. Field of the Invention

The present invention relates to an apparatus for determining an activated condition of an oxygen sensor.

2. Description of the Related Art

In an internal combustion engine for obtaining a desired air-fuel ratio, an oxygen sensor, such as a lean sensor, is used for obtaining an output signal which corresponds to the density of the oxygen of the exhaust gas from the engine. The output signal from the oxygen sensor controls a duration of a time of the opening of the fuel injector, to obtain an air-fuel ratio of the internal combustion engine set to a value larger than the stoichiometric air-fuel ratio.

A known oxygen sensor includes a body of a solid electrolyte, such as a stabilized zirconia, a first air permeable electrode on one side of the solid electrolyte body and in contact with the exhaust gas to be detected, and a second air permeable electrode on the other side of the solid electrolyte body and in contact with the reference gas, such as atmospheric air.

In this type of sensor, an application of a direct current electric voltage within a predetermined range across the electrodes obtains an electric current, called a limit electric current, which is maintained at a predetermined value in accordance with a density of the oxygen in the exhaust gas. Therefore, the detection of the output electric current from the oxygen sensor enables a value of the density of the exhaust gas to be obtained, and using this value, it is possible to estimate the value at which the air-fuel ratio for the internal combustion engine should be set.

Nevertheless, a low temperature of the solid electrolyte body (i.e., element temperature) in this type of oxygen sensor causes the sensor output value to be reduced while maintaining the same air-fuel ratio within a range at which it is used. Namely, the electric current value obtained corresponds to an oxygen density value which is lower than the actual value of the oxygen density, and as a result, a feed-back control of the air-fuel ratio in accordance with the output signal from the sensor during a low temperature state of the element causes the air-fuel ratio to be incorrectly controlled to a value larger than the preset air-fuel ratio.

One solution to such a problem is to provide a means of determining if a state is reached wherein the oxygen sensor is "fully activated", before executing the feed-back control of the air-fuel ratio. A prior art method of obtaining such a determination of the activated condition of the oxygen sensor uses the output level from the oxygen sensor when the engine is under a fuel cut (F/C) condition. This technique employs a principle such that the oxygen density of the exhaust gas during the fuel cut operation is equal to the oxygen density of the atmospheric air, and a determination of whether or not the oxygen sensor is in an activated state is obtained by determining if the output level from the oxygen sensor corresponds to the oxygen density of the atmospheric air. (See Japanese Unexamined Patent Publication No. 59-46350.) In this prior art, a threshold level is provided and it is determined whether the output level from the oxygen sensor has become higher than the threshold level during the fuel cut condition. When the output level from the oxygen sensor is higher than the threshold level, it is determined that the element temperature is high enough to ensure that the oxygen sensor is in an activated condition.

To improve the precision of the determination of the activated state of the oxygen sensor, a technique has been proposed whereby it is determined whether a condition, wherein the output level from the oxygen sensor is higher than the threshold value during the fuel cut condition, is continued. (See Japanese Unexamined Patent Publication No. 60-21265.) In this prior art, a measurement of the output of the oxygen sensor is repeatedly carried out at predetermined intervals during the fuel cut condition, and a determination of the activated state of the oxygen sensor is obtained when a continuation of a state wherein the output level of the oxygen sensor is higher than the threshold value for longer than a predetermined interval is determined.

In this prior art, the reason for the determination of the continuation of the state wherein the output level of the oxygen sensor is higher than the threshold value for longer than the predetermined interval, is to obtain a determination of the activated condition of the oxygen sensor as quickly as possible without losing the precision of the determination. The threshold value for determining the activation condition is usually the lowest possible value for obtaining a quick determination of the activated condition of the element, and thus an incorrect determination is apt to be made, since inevitably some fluctuation of the output level from the oxygen sensor will occur, which causes a situation to arise such that the output level from the oxygen is higher than the threshold value even if the sensor is not actually activated. Such an incorrect determination due to the fluctuation of the output level is avoided by determining if the sensor output level remains higher than the fixed value for a time longer than a predetermined interval.

The above-mentioned prior art suffers from a drawback in that a proper determination of the activated condition of the oxygen sensor cannot be always obtained, for the following reason. Where the engine is in a cruising state, e.g., when running on a freeway, if a steady state condition continues for a relatively long time, a fuel cut operation occurs only rarely. In this case, the prior art method of determining the activated state of the oxygen sensor by the detection of duration of the state where the sensor level is higher than a predetermined level for longer than the predetermined interval during the fuel cut operation, may sometimes cause the air-fuel ratio feedback control to be stopped for a relatively long time, and thus a precise control of the air-fuel ratio cannot be obtained.

SUMMARY OF THE INVENTION

An object of the present invention is to provide a device for obtaining a quick and precise determination of a thermally activated condition of the oxygen sensor, which increases the occurrences of the air-fuel ratio feedback control operation, to obtain a precise control of the air-fuel ratio to the desired value.

According to the first aspect of the present invention, a device is provided for determining an activated condition of an oxygen sensor for an internal combustion engine where a fuel cut operation is carried out under a predetermined condition of the engine, said device comprising:

means for detecting a state where the fuel cut operation is carried out;

a first comparing means for comparing the detected level of the sensor means with a predetermined first value when the engine is under a fuel cut condition;

a second comparing means for comparing the detected level of the sensor means with a predetermined second value which is lower than said first value when the engine is under a fuel cut condition;

a first determining means for determining an activated condition of the oxygen sensor when the first comparing means determines that the detected level once exceeds the first value, and;

a second determining means for determining an activated condition of the oxygen sensor when the second comparing means determines that the detected level consecutively exceeds the second value at least twice.

According to the second aspect of the present invention, an internal combustion engine is provided, comprising:

an engine body;

an intake line connected to the engine body for an introduction of intake air into the engine body;

a means for introducing an amount of fuel into the intake line for forming an air-fuel mixture;

an exhaust line connected to the engine body for a removal of a resultant exhaust gas from the engine body;

a means arranged in the exhaust line and responsive to the oxygen density of the oxygen in the exhaust gas for producing an electric signal having a level which indicates the air-fuel ratio of the combustible air-fuel mixture introduced into the engine;

a means, responsive to the signal from the sensor means, for controlling the amount of the supplied fuel, to thereby control the air-fuel ratio to a predetermined value;

a means, responsive to a predetermined condition of the engine, for cutting the supply of fuel to the engine;

a means for cutting the supply of fuel to the engine from the fuel supply means;

a first comparing means for comparing the detected level of the sensor means with a predetermined first value when the engine is under a fuel cut condition;

a second comparing means for comparing the detected level of the sensor means with a predetermined second value which is lower than said first value when the engine is under a fuel cut condition;

a first determining means for determining an activated condition of the oxygen sensor when the first comparing means determines that the detected level once exceeds the first value;

a second determining means for determining an activated condition of the oxygen sensor when the second comparing means determines that the detected level consecutively exceeds the second value at least twice, and;

means for allowing the feed-back control of the air-fuel ratio to be carried out by the control means when a determination of the activated condition of the oxygen sensor by at least one of the first and second determining means is obtained.

DESCRIPTION OF A PREFERRED EMBODIMENT

Figure 1:
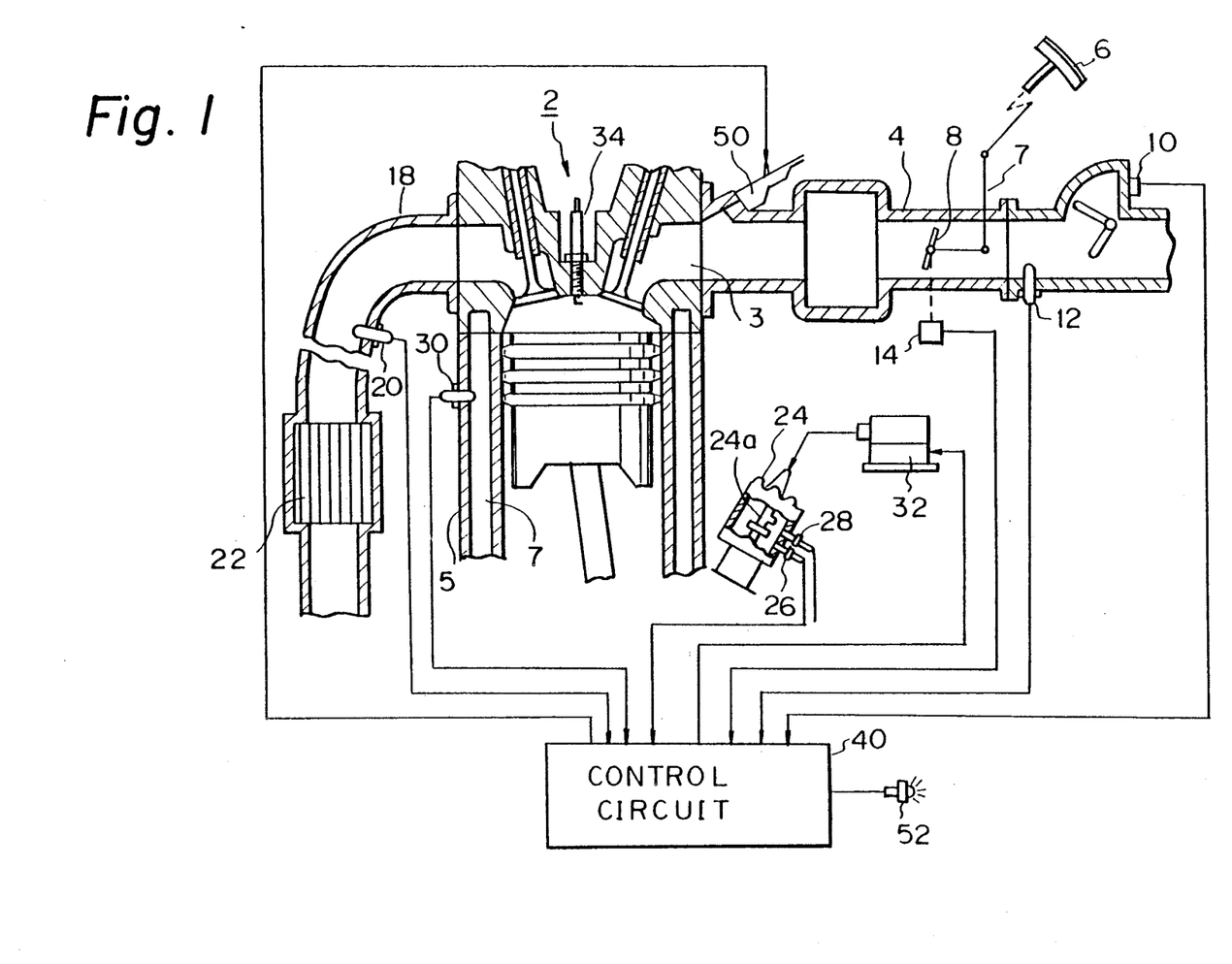
FIG. 1 is a schematic view of the internal combustion engine according to the present invention.

FIG. 1 shows an internal combustion engine 2 according to the present invention, which includes an intake pipe 4 in which a throttle valve 8 is arranged. The throttle valve 8 is connected to an accelerator pedal 6 by a link 7, and thus a degree of opening of the throttle valve 8 is controlled in accordance with a depression of the accelerator pedal 6. An air-flow meter 10 for detecting an amount of air introduced into the engine is arranged in the intake pipe 4 upstream of the throttle valve 8. A sensor 12 for detecting the temperature of intake air introduced into the engine is arranged in the intake pipe 4 between the throttle valve 8 and the air-flow meter 10, and a throttle position sensor 14 is connected to the throttle valve 8. The sensor 14 comprises a sensor for detecting a continuously varied degree of opening of the throttle valve 8, and an idling switch which is made ON when the throttle valve 8 is in the idling position and is made OFF when the throttle valve 8 is opened from the idling position.

An oxygen sensor 20 (i.e., lean sensor) is arranged in the exhaust pipe 18 for detecting an air-fuel ratio of the combustible mixture introduced into the engine, in response to an oxygen density of the exhaust gas in the exhaust pipe 18. A catalytic converter 22 is arranged in the exhaust pipe 18 downstream of the oxygen sensor 20.

Reference numeral 24 denotes a distributor having a distributor shaft 24a connected to a crankshaft of the engine. The distributor 24 is connected to an ignitor 32, and a spark plug 34 is arranged on a cylinder head and a high voltage electric current is supplied to the spark plug 34 from the ignitor 32 via the distributor 24, for carrying out an ignition of fuel.

A fuel injector 50 is arranged in the intake pipe 4 to generate a flow of injected fuel directed into an intake port 3 of the engine.

To detect various engine operating parameters, in addition to the above-mentioned air flow meter 10, an intake air temperature sensor 12, a throttle position sensor 14 and the oxygen sensor 20, the internal combustion engine 2 is provided with a first crank angle sensor 26 facing the distributor shaft 24a and outputting a pulse signal at every 30 degrees rotation of the crankshaft of the engine, to calculate the engine rotational speed NE, a second crank angle sensor 28 also facing the distributor shaft 24a and outputting a pulse signal at every 720 degrees rotation of the crank shaft, to determine a cylinder number, and a sensor 30 mounted on the cylinder block 5 body of the engine and in contact with cooling water in a water jacket 7 of the engine, for detecting the temperature of the cooling water for the engine 2.

These sensors are connected to an electronic control unit 40, which is a microcomputer system, and signals from the sensors are input to the unit 40.

Figure 2:
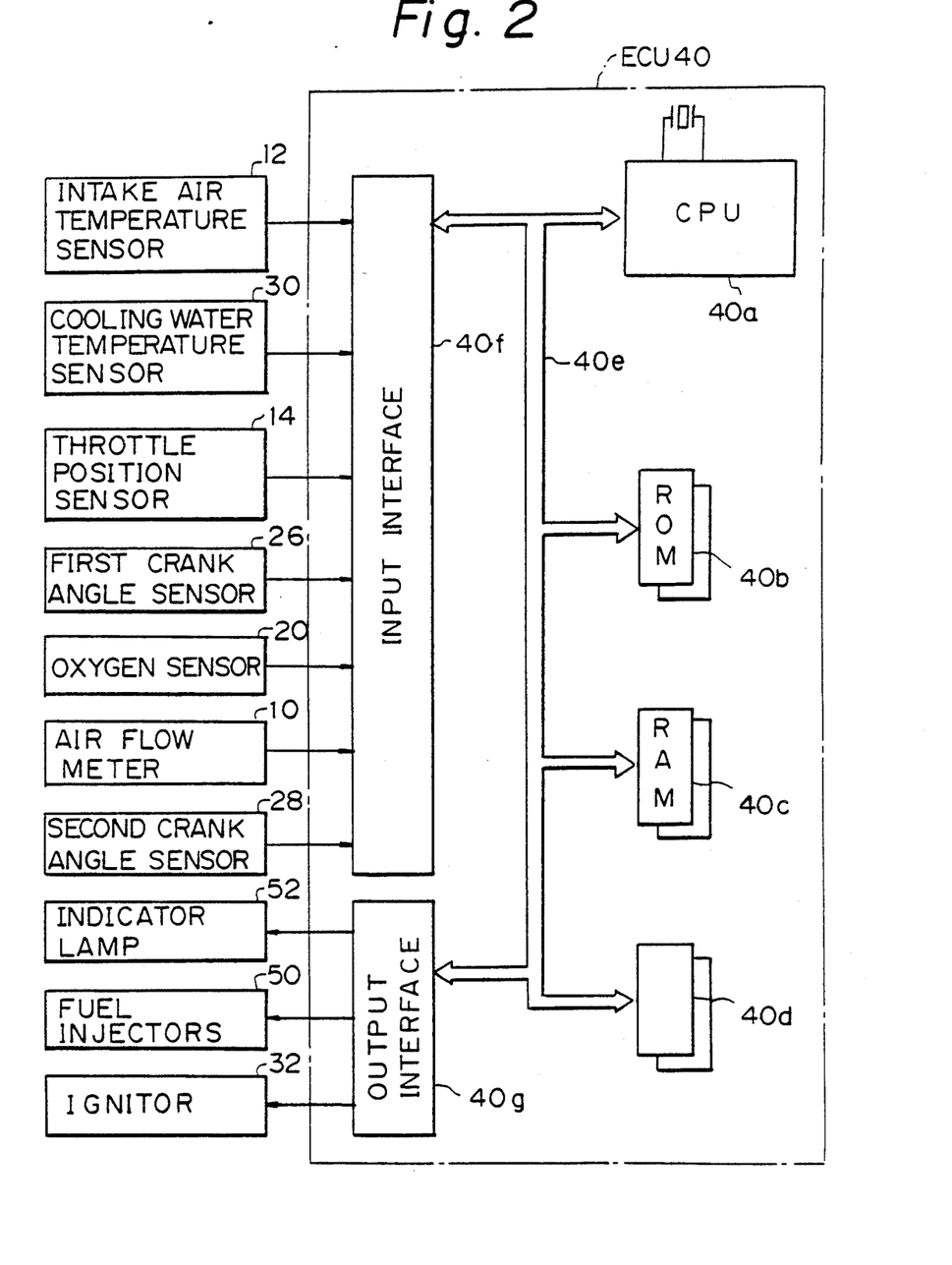
FIG. 2 is a schematic view of a control circuit shown in FIG. 1.

As shown in FIG. 2, the electronic control unit 40 includes a central processing unit (CPU) 40a, a read only memory (ROM) 40b for storing various programs and data such as values of a threshold level for determining an activated condition of the oxygen sensor 20, a random access memory (RAM) 40c as a means for temporarily storing programs and data, and a back-up RAM 40d which is always supplied with power by a battery (not shown) so that data is not erased if a main power supply is cut. A bus 40e interconnects these elements. The electronic control unit 40 is further provided with a input interface 40f and an output interface 40g, and the air flow meter 10, intake air temperature sensor 12, throttle position sensor 14, oxygen sensor 20, first and second crank angle sensors 26 and 28, and engine cooling water temperature sensor 30 are connected to the input interface 40f. Also, in addition to an ignitor 32 and fuel injectors 50, an indicator 52 is connected to the output interface 40g, to indicate whether the oxygen sensor 20 is activated.

The electronic control unit 40, which is responsive to various engine operating conditions detected by the sensors, executes the control of the amount of the fuel injected from the fuel injectors 50 and a control of the ignition timing by the ignitor 32. Furthermore, the electronic control unit 40 monitors the output level of the oxygen sensor 20, for determining an activated condition of the oxygen sensor 20 according to the present invention.

Figure 3:
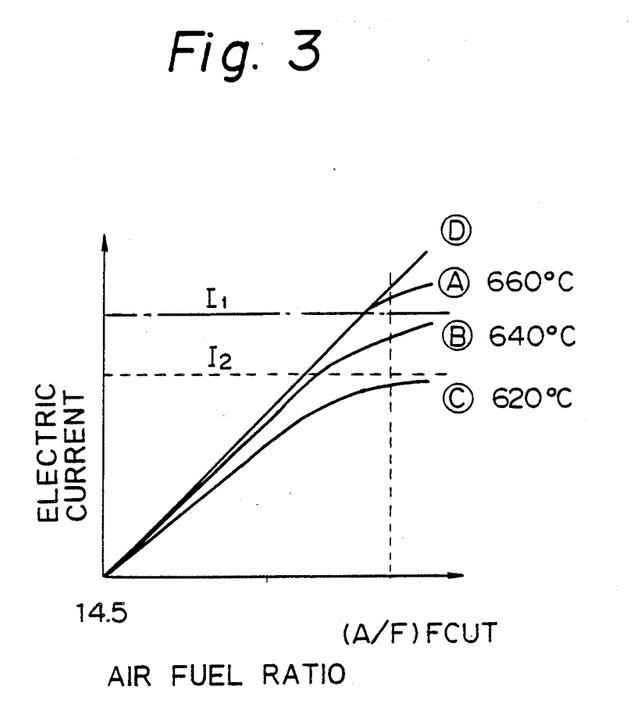
FIG. 3 shows a relationship between the air-fuel ratio and an output level from the oxygen sensor.

FIG. 3 shows the relationships between the air-fuel ratio of the combustible mixture introduced into the engine and an output electric current obtained by the oxygen sensor 20 arranged in the exhaust pipe 18. A curve D shows a linear relationship between the air-fuel ratio and the output current, obtained when the sensor 20 is completely activated. Curves A, B and C show the same relationships obtained when the sensor element temperature is 660° C., 640° C., and 620° C., respectively. According to the present invention, two different values of reference levels $I_1$ and $I_2$ are provided. When the output level from the oxygen sensor 20 once exceeds the higher reference value $I_1$, it is determined that the sensor 20 is activated. Contrary to this, when the output level of the sensor 20 exceeds only the lower reference revel $I_2$, the determination of the activated condition of the oxygen sensor 20 is obtained when this occurs twice in succession. Accordingly, a precise and quick determination of the activated condition of the oxygen sensor 20 can be obtained.

The determination of the activated condition of the oxygen sensor by any one of the first and the second reference values $I_1$ and $I_2$ allows the determination to be made quickly and precisely. Namely, the determination of the activated condition of the oxygen sensor is obtained when the detected value of the electric current from the oxygen sensor 20 under the fuel cut condition, where the gas to be detected has the same air-fuel ratio as that of the atmospheric air, is once higher than the higher reference value $I_1$ or is twice in succession higher than the lower reference $I_2$. As shown in FIG. 3, the higher reference value $I_1$, with respect to the air-fuel ratio during the fuel cut condition, $(A/F)_{FCUT}$, corresponding to the oxygen density of the atmospheric air, is between a value of the electric current on the curve A and a value of the electric current on the curve B. The lower reference value $I_2$, with respect to the air-fuel ratio during the fuel cut condition, $(A/F)_{FCUT}$, corresponding to the oxygen density of the atmospheric air, is between a value of the electric current on the curve B and a value of the electric current on the curve C.

Figure 4:
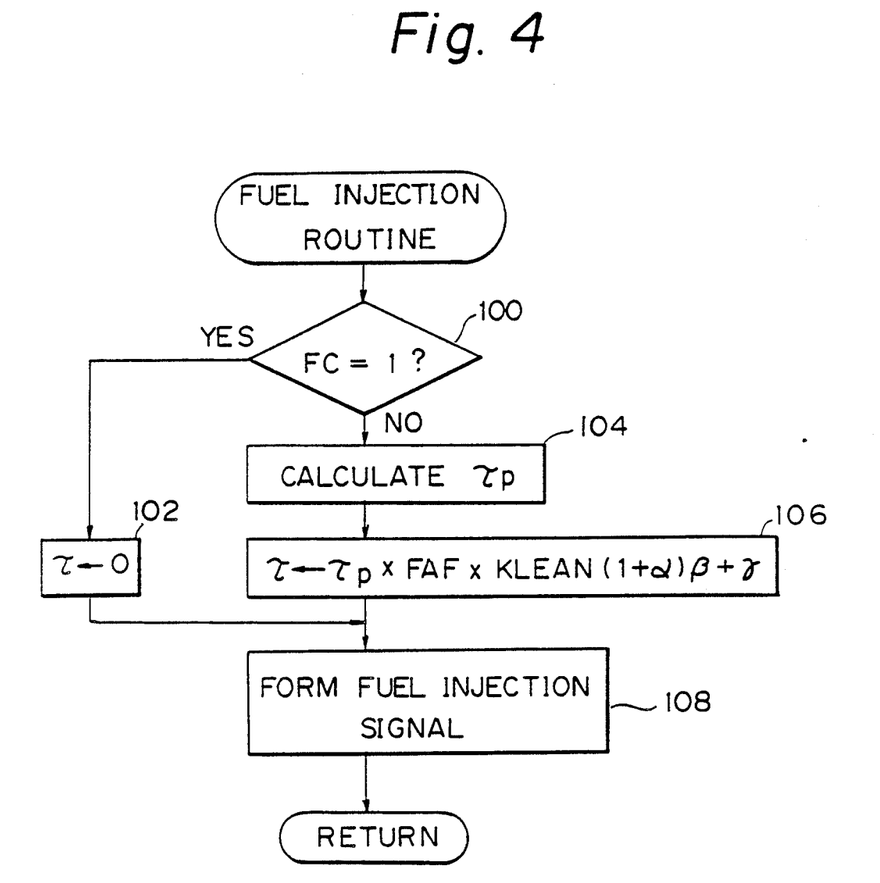
FIGS. 4 to 7 are flow charts showing the operation of the control circuit shown in FIG. 2.

Now, an air-fuel ratio control operation of the electronic control unit 40 will be described with reference to the flowcharts shown by FIGS. 4 to 7. The fuel injection can be independently carried out at desired timings in one cycle of the engine. FIG. 4 shows a fuel injection routine for each of the injectors 50, which is executed during one operation cycle of the engine. As is well known, this timing is detected by the number of a counter (not shown), which is incremented at every 30 degrees pulse signal output from the first crank angle sensor 26 and cleared at every 720 degrees pulse signal output from the second crank angle sensor 28. The routine in FIG. 4 is commenced at this timing, and at step 100 it is determined if the flag FC is set. As will be described later, the flag FC is set at (1) when the engine is under a fuel cut operation, and is reset to (0) when the engine has finished the fuel cut operation. When it is determined that the engine is under the fuel cut condition (FC=1), the routine goes to step 102 and a zero value is moved to a fuel injection amount $\tau$, whereby the fuel cut operation is carried out.

When engine is not under a fuel cut operation (FC=0), the routine goes from step 100 to step 104, where a basic fuel injection amount $\tau_p$ is calculated by $$\tau_p = K \times (Q/N),$$

where Q is an intake air amount detected by the air-flow meter, and N is engine speed calculated as a time difference between adjacent 30 degrees pulses from the first crank angle sensor 26. This basic fuel injection amount $\tau_p$ is used for obtaining a theoretical air-fuel ratio at the detected Q and N.

At step 106, a final fuel injection amount $\tau$ is calculated by $$\tau = \tau_p \times FAF \times KLEAN \times (1+\alpha)\beta + \gamma,$$

where FAF is a feedback correction factor, as will be described later, KLEAN is lean correction factor as will be also described later, and $\alpha$, $\beta$, and $\gamma$ are other correction amounts or correction factors applied to the calculation of the fuel injection amount, a detailed explanation of which is omitted since they are not closely related to the invention.

At step 108, a fuel injection signal is sent from the output portion 40g to the fuel injector 50, for carrying out a fuel injection operation, and an amount of fuel calculated at step 106 is injected into the engine.

Figure 5:
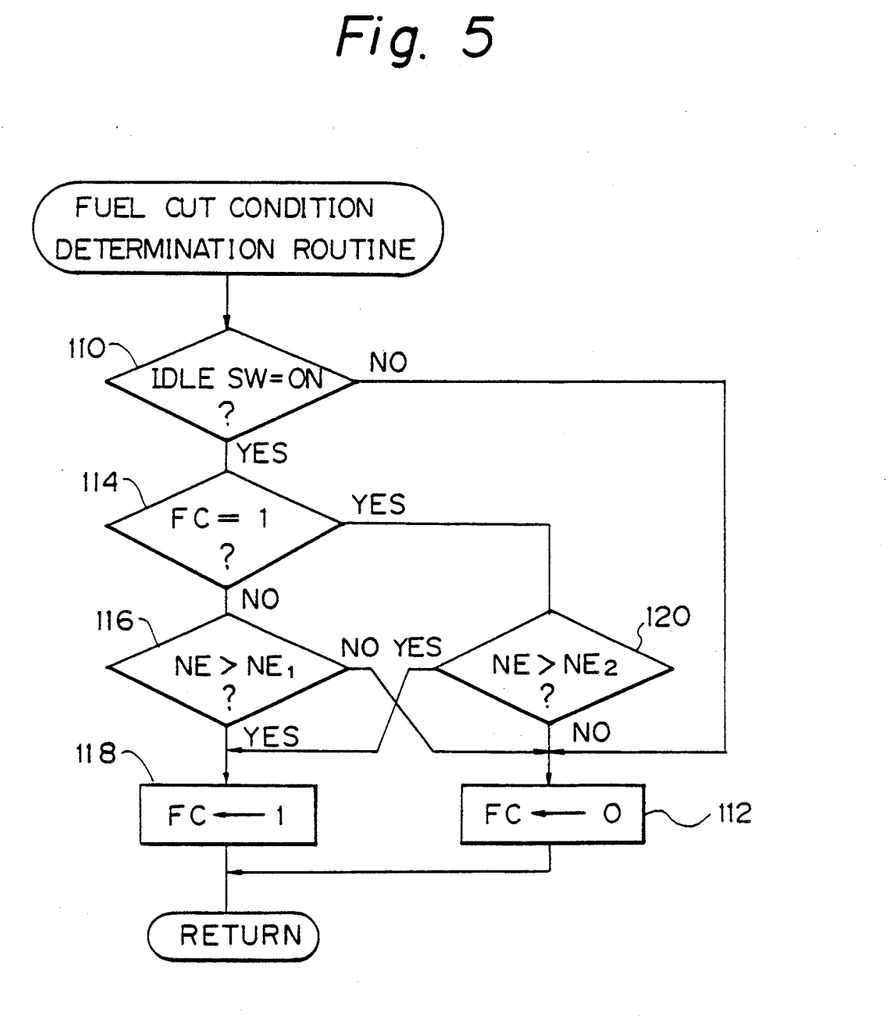

FIG. 5 shows a fuel cut condition determination routine, which is executed at a predetermined interval. At step 110, it is determined if the idle switch of the throttle position sensor 14 is ON, i.e., the throttle valve 8 is in the idling position. When it is determined that the idle switch is OFF, the routine goes to step 112 and the fuel cut flag FC is cleared (0). When it is determined that the idling switch is ON, the routine goes to step 114 and it is determined whether the fuel cut flag FC is set to (1). When FC=0, i.e., a fuel cut operation is not carried out during the timing at which this routine is carried out in the preceding routine, the routine goes to step 116 and it is determined whether the engine speed NE is larger than a predetermined value $NE_1$. When $NE > NE_1$, this means that the engine has been decelerated from a condition wherein the engine speed was higher than $NE_1$. The routine then goes to step 118 and the fuel cut flag FC is set to (1), and therefore, a fuel cut operation is carried out (step 102 in FIG. 4).

At the following timing for executing the routine of FIG. 5, the routine goes from step 114 to step 120 and it is determined whether the engine speed NE is larger than a predetermined value $NE_2$, which is smaller than $NE_1$. When it is determined that $NE>NE_2$, the routine goes to step 118 and the fuel cut operation is maintained. When the engine speed dropped below the level of $NE_2$, the routine goes from step 120 to the step 112, and the fuel cut operation is cancelled.

Figure 6:
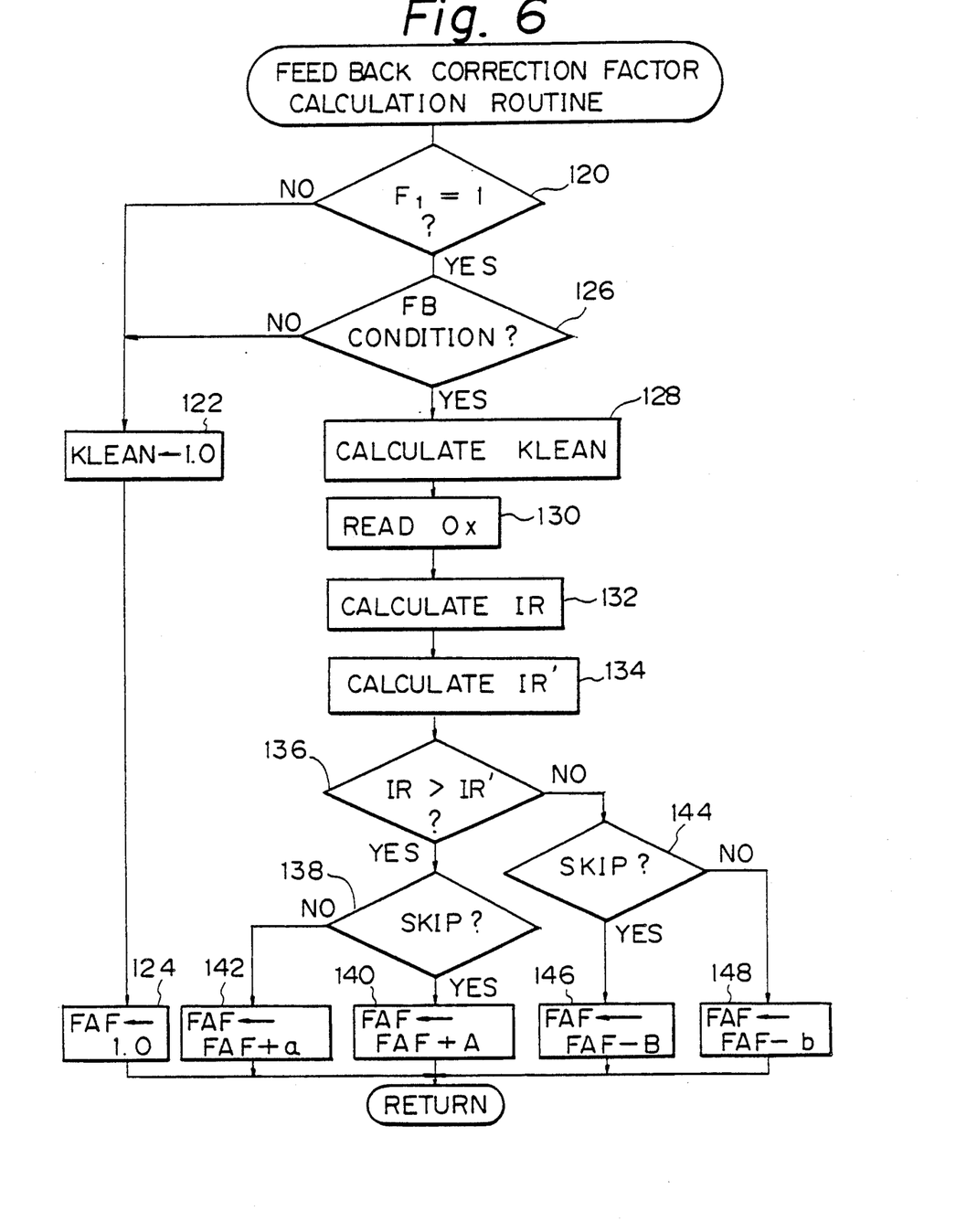

FIG. 6 shows a feedback correction factor calculation routine which is executed at predetermined intervals such as 4 milliseconds. At step 120, it is determined if a flag $F_1$ is set. As will be explained later, this flag is set at (1) when the oxygen sensor 20 is in an activated condition, and is reset to (0) when the oxygen sensor 20 is not activated. When the oxygen sensor 20 is not activated ($F_1=0$), the routine goes to step 122, and the steps following step 122 to execute the open loop control. During the open loop control, at step 122, a value of 1.0 is moved to the lean correction factor KLEAN, and the flow goes to step 124 where a value of 1.0 is moved to the feedback correction factor FAF. Because KLEAN=1.0, as a result of the execution of the open loop control, the air-fuel ratio is basically determined by the basic fuel amount $\tau_p$ calculated at step 106 in FIG. 4.

When it is determined that the oxygen sensor 20 is activated at step 120 ($F_1=1$), the routine goes to step 126 and it is determined if other feedback conditions are satisfied. The feedback control is stopped when, for example, the engine is under an acceleration condition. When the feed back condition is not satisfied, the routine goes from step 126 to step 122, and the steps following step 122, to execute the open loop control of the air-fuel ratio. When it is determined that the feedback conditions are satisfied, the routine goes to step 128 and a lean correction factor KLEAN is calculated. The lean correction factor may have values lower than 1.0, and as shown in the step 106 in FIG. 4, is multiplied with the basic fuel amount $\tau_p$, to obtain a lean air fuel mixture. As is well known, a map of data of the values of the lean correction factor with respect to combinations of the engine speed NE and engine load, such as a ratio of the intake air amount Q to the engine speed NE is provided. A well known map interpolation calculation of a value of the lean correction factor KLEAN is carried out by using the detected values of NE and Q/NE. At step 130, the value of the electric current Ox from the oxygen sensor 20 is input, and at step 132, a corrected electric current IR, which indicates the air-fuel ratio of the combustible mixture, is calculated from the detected electric current by the oxygen sensor 20. The two-dimensional map provided has the values of the IR with respect to the detected electric current, and at step 134, a reference value IR' of the corrected electric current, i.e., a target value of the air-fuel ratio, is calculated from the lean correction factor KLEAN calculated at step 128.

The processes of steps 136 to 148 generally show a air-fuel ratio feedback routine. At step 136, it is determined if the IR (corresponding to the detected air-fuel ratio) is larger than the IR' (corresponding to the target air-fuel ratio). When it is determined that $IR>IR'$, i.e., the detected air-fuel ratio is higher than the target air-fuel ratio, the routine goes to step 138 and it is determined if the first determination of $IR>IR'$ at step 136 is obtained. If the result of the determination at the step 138 is yes, the routine goes to step 140 and the feedback correction factor FAF is incremented for a value of A, i.e., a skip operation is carried out. When it is determined that the result of $IR>IR'$ at step 136 is not the first result, the routine goes to step 142 and the feedback correction factor FAF is incremented for a value of a, which is smaller than A. When it is determined that $IR\leq IR'$, i.e., the detected air-fuel ratio is equal to or smaller than the target air-fuel ratio, the routine goes to step 144 and it is determined if the first determination of $IR\leq IR'$ at step 136 is obtained. If the result of the determination at the step 144 is yes, the routine goes to step 146 and the feedback correction factor FAF is decremented for a value of B, i.e., a skip operation is carried out. When it is determined that the result of $IR\leq IR'$ at step 136 is not the first result, the routine goes to step 148 and the feedback correction factor FAF is decremented for a value of b, which is smaller than B.

Figure 7:
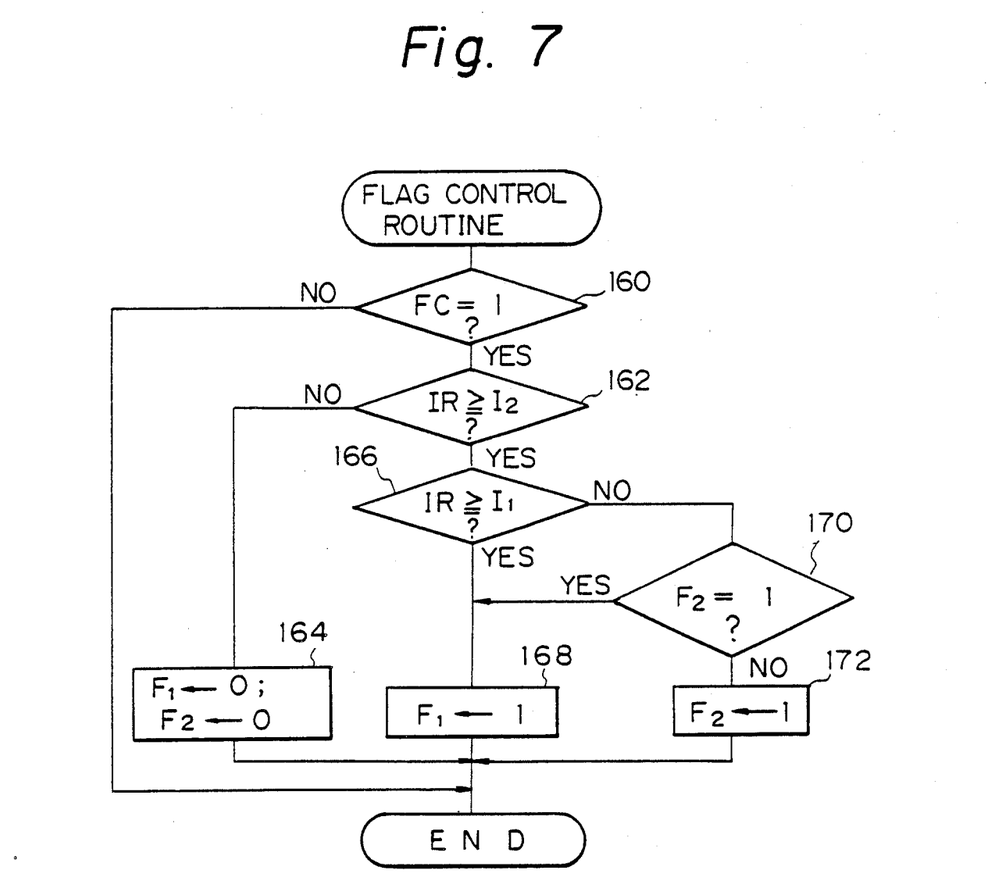

FIG. 7 shows a routine for determining an activated state of the oxygen sensor 20, and is carried out at a predetermined interval of, for example, 2, 18 or 25 seconds. At step 160 it is determined if the fuel cut flag FC is set. When the FC=0, i.e., the fuel cut operation is not carried out, the routine following step 162 is by-passed. When it is determined that the FC=1, i.e., the fuel cut operation is being carried out, the routine goes to step 162 and it is determined if the corrected output current IR from the oxygen sensor 20 is larger than a predetermined second or lower level $I_2$. As will be described later, when two consecutive determinations of $IR>I_2$ are obtained, a determination of an activated condition of the oxygen sensor 20 is obtained even if the output current IR does not exceed the higher or first level $I_1$. When it is determined that the IR is lower than the lower level, i.e., the oxygen sensor 20 is not activated, the routine goes to step 164 and the flags $F_1$, $F_2$ are cleared. When the flag $F_1$ is cleared ($F_1=0$), the routine at step 120 in FIG. 6 flows to steps 122 and 124, and therefore, the feedback control of the air-fuel ratio is not carried out, and thus an open control of the air-fuel ratio is carried out to obtain the theoretical air-fuel ratio. When it is determined that $IR>I_2$ at step 162 in FIG. 7, the routine goes to step 166 and it is determined whether the corrected output current IR from the oxygen sensor 20 is larger than a predetermined first or higher level $I_1$. When it is determined that the IR is higher than the first or higher level $I_1$, i.e., the oxygen sensor 20 is activated, the routine goes to step 168 and the flags $F_1$ is set. When the flag $F_1$ is set ($F_1=1$), the routine at step 120 in FIG. 6 flows to steps 126 and 128, and therefore, the feedback control of the air-fuel ratio is carried out to obtain a lean air-fuel ratio in accordance with the engine operating condition. When it is determined that the IR is lower than the first or higher level $I_1$ but higher than the second or lower level $I_2$, the routine goes to step 170 and it is determined if the flag $F_2$ is set. When a result $F_2=0$ is obtained at step 170, i.e., when the first determination of $IR>I_2$ at the step 162 is obtained, the routine goes to step 172 and the flag $F_2$ is set and the flag $F_1$ is held in the reset state ($F_1=$) so that the open loop control of the air-fuel ratio is maintained. At the following timing for executing the routine in FIG. 7, if the condition $I_2<IR<I_1$ is maintained, the routine goes from step 170 to step 168 and the flag $F_1$ is set, whereby a determination of the activated condition of the oxygen sensor 20 is obtained and the feedback control is commenced.

As is clear from the above, when a result of a determination of the IR between $I_2$ and $I_1$ is obtained, a determination is made at step 170 if the temporary flag $F_2$ is set at the execution of this routine at the preceding timing. If the result of the determination at step 170 is no, then the temporary flag is set, and thus the result of the determination of the step 170 becomes yes and the flag $F_1$ is set if the result of the value of the IR between $I_2$ and $I_1$ is again obtained at the execution of the step 166 during the following timing of the execution of the routine. This means that the temporary flag $F_2$ is set when two consecutive determinations that the IR is between $I_2$ and $I_1$ are made, and if such two consecutive determinations are obtained, it is considered that the oxygen sensor is activated, and thus the air-fuel ratio feed back control is commenced. As a result, a precise and rapid determination of the activated state of the oxygen sensor can be obtained.

When the engine is operating under a continuous steady state for a relatively long time, such as running on a free way, a fuel cut operation rarely occurs, and thus the higher first threshold value $I_1$, which is determined only once, is effective for obtaining a quick determination of the activated condition of the oxygen sensor 20. The lower second threshold value $I_2$, which is used twice consecutively, is effective for a positive and quick determination of the activated condition of the oxygen sensor when the output value of the oxygen sensor as activated is relatively small, as when a cold engine is started.

Although an embodiment of the present invention is described above with reference to attached drawings, it is obvious that many modification and changes can be made by those skilled in this art without departing from the scope and spirit of the present invention.

What is claimed:

1. A device for determining an activated condition of an oxygen sensor for an internal combustion engine when a fuel cut operation is carried out under a predetermined condition of the engine, comprising:
    means for detecting a state in which the fuel cut operation is carried out;
    first comparing means for comparing a detected level of the sensor means with a predetermined first value when the engine is under a fuel cut condition;
    second comparing means for comparing a detected level of the sensor means with a predetermined second value which is lower than said first value when the engine is under a fuel cut condition;
    first determining means for determining an activated condition of the oxygen sensor when the first comparing means determines that the detected level once exceeds the first value, and;
    second determination means for determining an activated condition of the oxygen sensor when the second comparing means determines that the detected level consecutively exceeds the second value at least twice.

2. An internal combustion engine comprising:
    an engine body;
    an intake line connected to the engine body for an introduction of intake air into the engine body;
    mean for introducing an amount of fuel into the intake line for forming an air-fuel mixture;
    an exhaust line connected to the engine body for a removal of a resultant exhaust gas from the engine body;
    means arranged in the exhaust line and responsive to the oxygen density of the oxygen in the exhaust gas for producing an electric signal having a level which indicates the air-fuel ratio of the combustible air-fuel mixture introduced into the engine;
    means, responsive to a signal from the sensor means, for controlling the amount of the supplied fuel to thereby control the air-fuel ratio to a predetermined value;
    means, responsive to a predetermined condition of the engine, for cutting the supply of fuel to the engine;
    means for cutting the supply of fuel to the engine from the fuel supply mean;
    first comparing means for comparing the detected level of the sensor means with a predetermined first value when the engine is under a fuel cut condition;
    second comparing means for comparing the detected level of the sensor means with a predetermined second value which is lower than said first value when the engine is under a fuel cut condition;
    first determining means for determining an activated condition of the oxygen sensor when the first comparing means determines that the detected level once exceeds the first value;
    second determining means for determining an activated condition of the oxygen sensor when the second comparing means determines that the detected level consecutively exceeds the second value at least twice, and;
    means for allowing a feed-back control of the air-fuel ratio to be carried out by the control means when the determination of the activated condition of the oxygen sensor by one of the first and second determination means is obtained.

3. An internal combustion engine according to claim 2, wherein said sensor means is a lean sensor capable of producing an electric signal having a level which is continuously varied in accordance the air-fuel ratio.

* * * * *